US012312558B2

United States Patent
Okamura

(10) Patent No.: US 12,312,558 B2
(45) Date of Patent: May 27, 2025

(54) ANTI-STAINING AGENT

(71) Applicant: KAO CORPORATION, Tokyo (JP)

(72) Inventor: Satoru Okamura, Wakayama (JP)

(73) Assignee: KAO CORPORATION, Tokyo (JP)

( * ) Notice: Subject to any disclaimer, the term of this patent is extended or adjusted under 35 U.S.C. 154(b) by 10 days.

(21) Appl. No.: 18/031,374

(22) PCT Filed: Dec. 14, 2021

(86) PCT No.: PCT/JP2021/045919
§ 371 (c)(1),
(2) Date: Apr. 12, 2023

(87) PCT Pub. No.: WO2022/138304
PCT Pub. Date: Jun. 30, 2022

(65) Prior Publication Data
US 2023/0374410 A1    Nov. 23, 2023

(30) Foreign Application Priority Data

Dec. 24, 2020   (JP) ................................ 2020-214764

(51) Int. Cl.
*C11D 1/12* (2006.01)
*C07C 309/17* (2006.01)

(52) U.S. Cl.
CPC ............ *C11D 1/123* (2013.01); *C07C 309/17* (2013.01); *C11D 2111/14* (2024.01)

(58) Field of Classification Search
CPC ........... C11D 3/43; C11D 1/83; C11D 3/2068; C11D 1/831; C11D 3/0026; C11D 3/0094; C11D 1/29; C11D 1/662; C11D 1/92; C11D 1/123; C11D 1/75; C11D 17/0043; C11D 1/94; C11D 1/02; C11D 1/72; C09K 23/017; C09K 23/10; C09K 23/16; C09K 23/04; C09K 23/56; A61Q 19/10; A61K 8/345; A61K 8/046; A61K 8/463; A61K 8/602; A61K 8/466; A61K 8/39
See application file for complete search history.

(56) References Cited

U.S. PATENT DOCUMENTS

| | | |
|---|---|---|
| 2,028,091 A | 1/1936 | Jaeger |
| 10,538,724 B2 | 1/2020 | Bittner et al. |
| 2006/0019851 A1 | 1/2006 | Hecht et al. |
| 2007/0214999 A1 | 9/2007 | Meyer et al. |
| 2018/0051201 A1 | 2/2018 | Vanzin et al. |

FOREIGN PATENT DOCUMENTS

| | | | |
|---|---|---|---|
| CN | 109072129 A | 12/2018 | |
| EP | 0071412 A1 | 2/1983 | |
| EP | 4122373 A1 | 1/2023 | |
| JP | S58-24555 A | 2/1983 | |
| JP | 2010083927 A | 4/2010 | |
| JP | 2015124297 A | 7/2015 | |
| JP | 2017214554 A | 12/2017 | |
| JP | 2020059817 A | 4/2020 | |
| JP | 2021147617 A | 9/2021 | |
| WO | WO-2017204149 A1 * | 11/2017 | ............... C11D 1/28 |

OTHER PUBLICATIONS

English translation of the International Preliminary Report on Patentabilty and Written Opinion issued Jul. 6, 2023 in PCT/JP2021/045919, 7 pages.
International Search Report issued Jan. 18, 2022 in PCT/JP2021/045919 (with English translation), 4 pages.
Teruo Tsunoda, "Physical Chemistry of Polymer Surface", vol. 17, No. 196, Central Research Laboratory, Hitachi, Ltd., 1968, 680-687 (with partial English translation).
Extended European Search Report issued Jan. 13, 2025, in corresponding European Patent Application No. 21910453.6, 8 pages.

* cited by examiner

*Primary Examiner* — Vishal V Vasisth
(74) *Attorney, Agent, or Firm* — Element IP, PLC

(57) ABSTRACT

The present invention is an anti-staining agent containing, (a) a sulfosuccinic acid branched alkyl ester in which the branched alkyl group is a branched alkyl group with 8 or more and 13 or less carbons [hereinafter referred to as component (a)]. Further, the present invention is an anti-staining method including bringing a treatment liquid into contact with an object to be treated, the treatment liquid containing component (a).

6 Claims, No Drawings

ANTI-STAINING AGENT

This application is a 371 of PCT/JP2021/045919, filed Dec. 14, 2021.

FIELD OF THE INVENTION

The present invention relates to an anti-staining agent and an anti-staining method.

BACKGROUND OF THE INVENTION

Situations in which hydrophobic surfaces come into contact with water exist everywhere. For example, in an ordinary household, in a situation where leftover water is left stored in the prefabricated bathtub for the next wash, oil components such as sebum or the like adhere to the bathtub's hydrophobic surface to stain the bath, or if oil stains adhere to the inside of the dishwashing machine, it also reduces washing efficiency. Further, hydrophobic materials such as polyvinyl chloride or the like are also used for pits and pipes that serve as water flow paths, and if there exist oil components, they adsorb to the hydrophobic materials and stain the surface of the hydrophobic materials. Therefore, there is a need for an anti-staining technology that inhibits the adsorption of oil components to hydrophobic surfaces that come into contact with water.

On the other hand, sulfosuccinic acid esters are known to have excellent washing performance and interfacial-active performance as a surfactant (for example, JP-A 2017-214554 and US-A 2007/0214999).

SUMMARY OF THE INVENTION

There is a need for a technology that inhibits the adsorption of hydrophobic stain components such as oil components or the like to hydrophobic surfaces that come into contact with water. Further, hydrophobic stain components that are dissolved in water by detergents may reattach to hydrophobic surfaces. Thus, for example, when resin tableware is washed in an automatic dishwashing machine, oil stains dissolved in water by the washing is transferred to the resin tableware, becoming one of the factors to reduce the level of satisfaction with stain removal.

The present invention provides an anti-staining agent and an anti-staining method for inhibiting the adsorption of oil components to the surfaces of treatment target objects.

The present invention relates to an anti-staining agent containing, (a) a sulfosuccinic acid branched alkyl ester in which the branched alkyl group is a branched alkyl group with 8 or more and 13 or less carbons [hereinafter referred to as component (a)].

Further, the present invention relates to an anti-staining method including bringing a treatment liquid into contact with an object to be treated, the treatment liquid containing, (a) a sulfosuccinic acid branched alkyl ester in which the branched alkyl group is a branched alkyl group with 8 or more and 13 or less carbons.

According to the present invention, provided are an anti-staining agent and an anti-staining method for inhibiting the adsorption of oil components to the surfaces of treatment target objects.

EMBODIMENTS OF THE INVENTION

As a result of careful consideration, the present inventors found that when specific compounds are brought into contact with treatment target objects, the adsorption of oil components to the surfaces of the treatment target objects is inhibited, and excellent anti-staining effects are exhibited, which led them to the completion of the present invention.

While the mechanism by which the anti-staining agent of the present invention inhibits the adsorption of oil components to the surfaces of treatment target objects is uncertain, it is considered that the anti-staining agent of the present invention adsorbs to the surfaces of treatment target objects and controls the surface energies of the treatment target objects (modifies the surfaces of the treatment target objects), thereby preventing the adsorption of oil components to the surfaces of the treatment target objects. According to the anti-staining agent and the anti-staining method of the present invention, not only are excellent anti-staining effects obtained if treatment target objects are treated in advance with the anti-staining agent of the present invention, but also stain components included in washing liquids or the like for treatment target objects are prevented from reattaching to the treatment target objects if the anti-staining agent of the present invention is included in the washing liquids or the like at a predetermined concentration. In particular, the anti-staining agent of the present invention can prevent oil components included in water from adsorbing to hydrophobic surfaces.

<Anti-Staining Agent>

The anti-staining agent of the present invention contains (a) a sulfosuccinic acid branched alkyl ester in which the branched alkyl group is a branched alkyl group with 8 or more and 13 or less carbons [hereinafter referred to as component (a)]. The anti-staining agent of the present invention may be an anti-staining agent containing component (a) as an active ingredient, for example, as an active ingredient for imparting anti-staining effects to target objects.

Component (a) is a sulfosuccinic acid branched alkyl ester in which the branched alkyl group is a branched alkyl group with 8 or more and 13 or less carbons. The sulfosuccinic acid branched alkyl ester of component (a) may also be a salt. In other words, component (a) may be one or more compounds selected from sulfosuccinic acid branched alkyl esters and salts thereof in which the branched alkyl group is a branched alkyl group with 8 or more and 13 or less carbons. Examples of the salts include inorganic salts such as sodium salts, potassium salts, ammonium salts, magnesium salts or the like, and organic salts such as monoethanolamine salts, diethanolamine salts, triethanolamine salts, morpholine salts or the like. The salts are preferably salts selected from sodium salts, potassium salts, ammonium salts, magnesium salts and monoethanolamine salts, more preferably inorganic salts selected from sodium salts and potassium salts, and further preferably sodium salts.

Examples of the ester of component (a) include a monoester and a diester. Component (a) is preferably a sulfosuccinic acid branched alkyl diester in which the branched alkyl groups are a branched alkyl group with 8 or more and 13 or less carbons.

The branched alkyl group of component (a) preferably has 8 or more and 11 or less carbons and particularly preferably has 9 or 10 carbons.

The branched alkyl group of component (a) is preferably a branched alkyl group having a main chain with 6 or 7 carbons and one or more side chains.

The branched alkyl group of component (a) is preferably a branched alkyl group having a main chain with 6 or 7 carbons and one or more side chains, the side chains having 3 or 4 carbons in total.

The branched alkyl group of component (a) is preferably a branched alkyl group selected from 2-propylheptyl group and 3,5,5-trimethylhexyl group.

Examples of component (a) include a sulfosuccinic acid branched alkyl ester represented by the following general formula (a1):

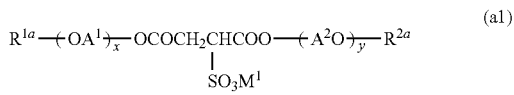

where $R^{1a}$ and $R^{2a}$ each independently represent a branched alkyl group with 8 or more and 13 or less carbons; $A^1$ and $A^2$ each independently represent an alkylene group with 2 or more and 4 or less carbons, and x and y represent an average number of added moles and each independently represent 0 or more and 6 or less; and $M^1$ represents a hydrogen atom or a cation.

Further, examples of component (a) include a sulfosuccinic acid branched alkyl ester represented by the general formula (a1-1) below. This compound is a compound of the general formula (a1) where x=0 and y=0.

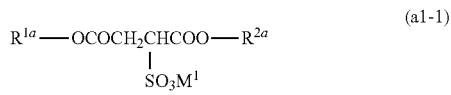

where $R^{1a}$ and $R^{2a}$ each independently represent a branched alkyl group with 8 or more and 13 or less carbons; and $M^1$ represents a hydrogen atom or a cation.

The following explanations can be applied to each of the general formulae (a1) and (a1-1).

$R^{1a}$ and $R^{2a}$ may have the same number or different numbers of carbons.

In the present invention, a hydrocarbon residue left after the removal of a hydroxyl group from a secondary alcohol is included in an open-chain branched hydrocarbon group.

In each of the open-chain branched hydrocarbon groups of $R^{1a}$ and $R^{2a}$ in the present invention, a hydrocarbon chain whose carbon number is the largest when counted from the carbon atom bonded to the oxygen atom is considered the main chain, and a hydrocarbon chain bonded to the main chain in a branching-off manner is considered a side chain.

When there are two or more possible main chains, in other words, when there are two or more hydrocarbon chains with the largest carbon number (hereinafter referred to also as the longest hydrocarbon chains), the main chain is determined in the following order:

1. a longest hydrocarbon chain from which a side chain having a larger number of carbon atoms branches off is considered the main chain;
2. next, when the side chains branching off from the longest hydrocarbon chains have the same number of carbon atoms, a longest hydrocarbon chain from which a larger number of side chains branch off is considered the main chain;
3. next, when the same number of side chains branches off from the longest hydrocarbon chains, a longest hydrocarbon chain having a side chain at a carbon atom which is closer to the oxygen atom when counted from the carbon atom bonded to the oxygen atom is considered the main chain; and
4. next, when the carbon atoms having side chains closest to the oxygen atom are in the same position, a longest hydrocarbon chain having a larger number of carbon atoms in the side chain closest to the oxygen atom is considered the main chain.

Note that when there are two or more longest hydrocarbon chains having the same symmetric structure, any of them may be considered the main chain.

In the branched alkyl groups of $R^{1a}$ and $R^{2a}$, the open-chain branched hydrocarbon groups may have the same number or different numbers of carbons in total, and each have 8 or more and preferably 9 or more, and 13 or less, preferably 11 or less and more preferably 10 or less carbons in total from the viewpoint of inhibiting the adsorption of oil components to hydrophobic surfaces.

In the branched alkyl groups of $R^{1a}$ and $R^{2a}$, the main chains may have the same number or different numbers of constituent carbons, and each have preferably 6 or 7 constituent carbons from the viewpoint of inhibiting the adsorption of oil components to hydrophobic surfaces.

In the branched alkyl groups of $R^{1a}$ and $R^{2a}$, the side chains may have the same number or different numbers of constituent carbons in total, and each have 2 or more and preferably 3 or 4 constituent carbons in total from the viewpoint of inhibiting the adsorption of oil components to hydrophobic surfaces.

In the present invention, the total number of carbons constituting side chains is the total of the carbon numbers of all the side chains other than the main chain in one branched alkyl group, and when there are two or more side chains, it refers to the total of the carbon numbers of all those side chains.

$R^{1a}$ and $R^{2a}$ may have the same number or different numbers of side chains and each have one or more and preferably 3 or less side chains from the viewpoint of inhibiting the adsorption of oil components to hydrophobic surfaces, and each have preferably one side chain when the side chain has 2 or more carbons and each have 2 or more and preferably 3 or 4 side chains when the side chains each have one carbon.

In the present invention, the number of side chains refers to the number of side chains branching off from the main chain, and even if the side chain further has a side chain branching off from the side chain, the number of side chains remains the same. However, a side chain may further have a side chain branching off from the side chain from the viewpoint of inhibiting the adsorption of oil components to hydrophobic surfaces.

$R^{1a}$ and $R^{2a}$ may have the same number or different numbers of branch carbons, and each have one or more, and preferably 3 or less and furthermore preferably 2 or less branch carbons from the viewpoint of inhibiting the adsorption of oil components to hydrophobic surfaces.

In the present invention, the number of branch carbons refers to the total of the number of tertiary carbon atoms and the number of quaternary carbon atoms in the open-chain branched hydrocarbon group.

In a preferable aspect of $R^{1a}$ and $R^{2a}$, the open-chain branched hydrocarbon groups of $R^{1a}$ and $R^{2a}$ each independently have 9 or 10 and preferably 10 carbons in total, the main chains each independently have 6 or 7 and preferably 7 carbons, the side chains each independently have 3 constituent carbons, and $R^{1a}$ and $R^{2a}$ each independently have one or more and 3 or less and preferably one side chain.

$R^{1a}$ and $R^{2a}$ may represent the same or different concrete branched alkyl groups, and each represent preferably a branched alkyl group selected from 2-ethylhexyl group, 2-propylheptyl group and 3,5,5-trimethylhexyl group and more preferably a branched alkyl group selected from 2-propylheptyl group and 3,5,5-trimethylhexyl group.

In the general formula (a1), $A^1$ and $A^2$ each independently represent an alkylene group with 2 or more, and 4 or less and preferably 3 or less carbons.

In the general formula (a1), x and y represent an average number of added moles, and each independently represent preferably 0 or more, and preferably 6 or less, more preferably 4 or less, further preferably 2 or less and further preferably 0 from the viewpoint of inhibiting the adsorption of oil components to hydrophobic surfaces.

Further, x+y is preferably 0 or more, and preferably 12 or less, more preferably 6 or less, further preferably 3 or less and further preferably 0 from the viewpoint of inhibiting the adsorption of oil components to hydrophobic surfaces.

$M^1$ represents a hydrogen ion, an inorganic cation such as a sodium ion, an ammonium ion, a potassium ion, a magnesium ion or the like, or an organic cation such as a monoethanolammonium ion, a diethanolammonium ion, a triethanolammonium ion, a morpholinium ion or the like, and represents preferably a cation selected from a sodium ion, an ammonium ion, a potassium ion, a magnesium ion and a monoethanolammonium ion, more preferably an inorganic cation selected from a sodium ion and a potassium ion, and further preferably a sodium ion.

While a method for preparing a compound that $R^{1a}$ and $R^{2a}$ are the same is not particularly limited, the compound can be produced, for example, by referring to a method described in U.S. Pat. No. 2,028,091, and as for a method for preparing an asymmetric compound that $R^{1a}$ and $R^{2a}$ are different, the compound can be produced, for example, by referring to JP-A S58-24555. As a raw material for component (a), a compound obtained by adding an alkylene oxide to an alcohol with a predetermined number of carbons can also be used.

Examples of a suitable alcohol used for the production of component (a) of the present invention include:
(1) a primary alcohol represented by 2-ethylhexanol, 3,5,5-trimethylhexane-1-ol, 2-propylheptan-1-ol or the like; and
(2) a secondary alcohol represented by 5-nonanol, 2,6-dimethyl-4-heptanol or the like.

The present invention can provide, by using component (a), an anti-staining agent excellent in the inhibition of the adsorption of oil components to hydrophobic surfaces.

Treatment target objects (objects to be treated) for the anti-staining agent of the present invention are not particularly limited to, but preferably hard articles and preferably hard articles having hydrophobic surfaces. Examples of the treatment target objects include, for example, articles formed of glass, metal, resin or the like.

In the hydrophobic surfaces, the surfaces that come in contact with stains may have critical surface energies of 50 mN/m or less. Further, the hydrophobic surfaces may be surfaces covered with polymers or the like. Specifically, while it is known that, for example, polyethylene has a surface energy of 35 mN/m, polypropylene has a surface energy of 21.0 to 28.5 mN/m, and polystyrene has a surface energy of 44 mN/m (Physical Chemistry of Polymer Surface, Vol. 17, No. 196, 1968, 680-687), the present invention can effectively impart anti-staining effects to hydrophobic surfaces having such surface energies.

The anti-staining agent of the present invention is suitable as anti-staining agents for use in bathrooms, sinks, washing tubs, tableware, cooking utensils and others, and among these, it is more suitable as an anti-staining agent for use in tableware and further as an anti-staining agent for use in the prevention of the adhesion of oil stains (solid fat or the like) to tableware. Further, the anti-staining agent of the present invention is preferably used as an anti-staining agent during dishwashing using automatic dishwashing machines, as it can prevent the reattachment of oil stains to tableware having hydrophobic surfaces and the adhesion of oil stains to the inside of automatic dishwashing machines. Note that the anti-staining agent of the present invention may be contained in a liquid detergent composition for use in automatic dishwashing machines.

If the anti-staining agent of the present invention is contained, for example, in a bathtub cleaning agent or a bathing agent, it can inhibit the adhesion of sebum stains or the like to bathtubs. Further, if the anti-staining agent of the present invention is contained in a fluid that flows through pipes, it can prevent the adhesion of stain components to the inside of the pipes.

Regardless of in which treatment liquid, for example, one before washing, during washing or during rinsing of tableware the anti-staining agent of the present invention is contained when the agent is used for tableware, it can attain the effects of the present invention, and can inhibit the reattachment of stain components (for example, oil stains such as solid fat, liquid oil or the like) to tableware.

The concentration of component (a) in the anti-staining agent of the present invention during use is preferably 1 ppm (on a mass basis, the same applies hereinafter) or more, more preferably 10 ppm or more and further preferably 20 ppm or more, and preferably 500 ppm or less, more preferably 300 ppm or less and further preferably 200 ppm or less from the viewpoint of inhibiting the adsorption of oil components to hydrophobic surfaces.

Note that, in the present invention, the descriptions about the amount of component (a) (ppm and mass %) are based on the mass of the compound converted to a sodium salt, for example, the mass given by assuming that $M^1$ in the general formula (a1) is sodium.

It is known that surfactants generally exhibit their interfacial-active performance at concentrations equal to or more than their critical micelle concentrations (hereinafter referred to as cmc). Surprisingly, as demonstrated in Examples later, a compound of the general formula (a1-1) in which $R^{1a}$ and $R^{2a}$ represent 2-propylheptyl, one aspect of component (a) of the present invention, which has a cmc of about 500 ppm (measured with pure water), attains excellent anti-staining effects even if the concentration of this compound is lower than the cmc of the compound. Therefore, the concentration of component (a) in the anti-staining agent of the present invention during use may be less than the cmc of component (a). In the present invention, a value obtained as an equilibrium value using a surface tension measurement method is employed as the cmc. The cmc may be an equilibrium value at 25° C. and under an atmospheric pressure (1013 hPa).

The anti-staining agent of the present invention may contain an optional component other than component (a) in a range that the effects of the present invention are not impaired. The anti-staining agent of the present invention can be formulated with a component such as a surfactant, a solvent, a hydrotropic agent, a dispersant, a pH adjuster, a thickener, a viscosity adjuster, a fragrance, a colorant, an antioxidant, a preservative, a defoamer, a bleaching agent, a bleach activator or the like as an optional component (provided that those qualified as component (a) are excluded).

The anti-staining agent of the present invention can be produced by mixing a predetermined amount of component (a) with water. In doing so, a precursor composition containing component (a) can be diluted with water to obtain the anti-staining agent composition of the present invention. For example, the anti-staining agent of the present invention may be prepared by carrying out such dilution immediately before using the anti-staining agent of the present invention. Examples of the precursor composition include, for example, a composition containing component (a) in an amount of preferably 0.01 mass % or more, more preferably 0.05 mass % or more and further preferably 0.1 mass % or more, and preferably 5 mass % or less and more preferably 3 mass % or less and further containing water.

The pH at 25° C. of the anti-staining agent of the present invention is preferably 2 or more, more preferably 4 or more and further preferably 5 or more, and preferably 10 or less, more preferably 9 or less and further preferably 8 or less from the viewpoint of irritation to hand skin. Note that the pH can be measured by a glass electrode method.

The viscosity at 25° C. of the anti-staining agent of the present invention is, for example, preferably 3 mPa·s or more and more preferably 10 mPa·s or more, and preferably 5,000 mPa·s or less and more preferably 2,500 mPa·s or less, though it depends on its applications or the like. The viscosity can be adjusted with a thickener, a solvent, a hydrotropic agent or the like commonly used.

In the present invention, a method of diluting the anti-staining agent of the present invention with water by a factor of 10 or more and less than 10,000 and preferably 50 or more and less than 5,000 to prepare the anti-staining agent composition (treatment liquid) and using the composition for treatment of an object to be treated is suitable.

The present invention provides use of (a) a sulfosuccinic acid branched alkyl ester in which the branched alkyl group is a branched alkyl group with 8 or more and 13 or less carbons [component (a)] as an anti-staining agent.

The present invention provides use of component (a) as an anti-staining agent for hydrophobic surfaces.

The present invention provides use of component (a) as an anti-staining agent for preventing the adhesion of oil components to hydrophobic surfaces.

The matters stated in the anti-staining agent of the present invention can be appropriately applied to theses uses.

<Anti-Staining Method>

The present invention provides an anti-staining method including bringing a treatment liquid into contact with an object to be treated, the treatment liquid containing component (a). The object to be treated is a treatment target article for the anti-staining agent of the present invention.

The treatment liquid of the present invention can be obtained by mixing the anti-staining agent of the present invention with water. Further, the treatment liquid of the present invention can be obtained by diluting the precursor composition containing component (a) with water. Further, the anti-staining agent of the present invention may be used as-is as the treatment liquid of the present invention.

The matters stated in the anti-staining agent of the present invention can be appropriately applied to the anti-staining method of the present invention. Specific examples and preferable aspects of component (a), anti-staining treatment targets, and others in the anti-staining method of the present invention are the same as those in the anti-staining agent of the present invention.

Treatment targets for the anti-staining method of the present invention are preferably surfaces of hard articles and preferably hard articles having hydrophobic surfaces. For example, treatment targets for the anti-staining method of the present invention may be hydrophobic surfaces of tableware or the like. Further, anti-staining target objects may be, for example, bathtubs, pipes, medical or optical instruments and others. In the present invention, a preferable anti-staining treatment target is tableware during washing of tableware using an automatic dishwashing machine and further during washing of tableware to which oil stains including solid fat adhere using an automatic dishwashing machine.

The automatic dishwashing machine may be any automatic dishwashing machine generally available on the market, and for example, either an automatic dishwashing machine for home use or an automatic dishwashing machine for commercial use may be used.

Washing conditions are not particularly limited, and washing temperature, washing time and others can conform to publicly-known washing conditions for automatic dishwashing machines.

The treatment liquid of the present invention contains preferably 1 ppm or more, more preferably 10 ppm or more and further preferably 20 ppm or more, and preferably 500 ppm or less, more preferably 300 ppm or less and further preferably 200 ppm or less of component (a) from the viewpoint of inhibiting the adsorption of oil components to hydrophobic surfaces. The treatment liquid of the present invention may contain component (a) at a concentration less than the cmc of component (a).

The pH of the treatment liquid of the present invention is preferably 2 or more, more preferably 4 or more and further preferably 5 or more, and preferably 10 or less, more preferably 9 or less and further preferably 8 or less from the viewpoint of irritation to hand skin. This pH is pH at a washing temperature.

In the washing method of the present invention, the washing temperature is preferably 40° C. or more and more preferably 50° C. or more from the viewpoint of washing performance, and preferably 80° C. or less and more preferably 70° C. or less from the viewpoints of washing performance and productivity. This washing temperature may be the temperature of the washing liquid of the present invention.

The content of component (a), washing time and washing temperature specified above are conditions that are also preferable, for example, for washing tableware in an automatic dishwashing machine.

After washed in an automatic dishwashing machine, tableware is usually promptly rinsed in the same automatic dishwashing machine with water, warm water or hot water, for example, hot water at 70° C. or more and 90° C. or less for 5 seconds or more and 15 seconds or less.

While a method for bringing the anti-staining agent of the present invention into contact with the object to be treated is not particularly limited, it can be carried out by application, immersion, spraying or the like. During the immersion of the object to be treated in the treatment liquid including the anti-staining agent of the present invention, mechanical force may be applied by stirring, shaking, water flow or the like, or using a tool commonly used for washing, such as a brush, a sponge or the like.

EXAMPLES

Component (a) or (a') listed below was dissolved in water with 3.5° DH to prepare the treatment liquids shown in Tables 1 to 3. Component (a') is a comparative component for component (a). Further, the pH of the treatment liquids was measured by a glass electrode method. The cmc values are those under an atmospheric pressure, at 25° C., with pure water and at a pH of 7.

Component (a)

The carbon numbers of branched alkyl groups are shown in the parentheses. a-1 is a sulfosuccinic acid branched alkyl ester synthesized using a branched alcohol commercially available as ISALCHEM123 (manufactured by Sasol Limited) (12 carbons/13 carbons=37-48/52-63 (mass ratio), a branching rate of 92 mass % or more (Sasol Limited's catalog value)).

- a-1 sodium di-(branched alkyl with 12 carbons/13 carbons) sulfosuccinate (in which the alkyl groups each have 12 or 13 carbons)
- a-2 sodium di-(2-propylheptyl) sulfosuccinate (in which one alkyl group has 10 carbons), cmc: about 500 ppm
- a-3 sodium di-(3,5,5-trimethylhexyl) sulfosuccinate (in which the alkyl groups each have 9 carbons), cmc: about 600 ppm
- a-4 sodium di-(2-ethylhexyl) sulfosuccinate (in which the alkyl groups each have 8 carbons), cmc: about 1100 ppm Component (a')

- a'-1 sodium di-(1,3-dimethylbutyl) sulfosuccinate (in which the alkyl groups each have 6 carbons), cmc: 3000 ppm or more a'-2 sodium dodecyl sulfate, cmc: about 2800 ppm
a'-3 sodium 1-dodecane sulfonate, cmc: about 3000 ppm
a'-4 sodium laurate, cmc: about 6000 ppm
a'-5 polyoxyethylene lauryl ether (product name: EMULGEN 106, manufactured by Kao Corporation), the average number of added moles of the ethyleneoxy group: 5, cmc: about 20 ppm
a'-6 7EO adduct of a secondary alcohol with 12 or more and 14 or less carbons (product name: SOFTANOL 70, manufactured by NIPPON SHOKUBAI CO., LTD.), EO: an ethyleneoxy group, cmc: about 40 ppm when the polypropylene plate is brought into contact with the treatment liquids including the anti-staining agents, high contact angles are attained. This result suggests that the anti-staining agent of the present invention reduces solid-liquid interfacial energy on hydrophobic surfaces, making oil stains such as liquid oil or the like less likely to adsorb to the hydrophobic surfaces.

In particular, it is understood that the treatment liquids including the anti-staining agents of the present invention can attain anti-staining effects even if they are very dilute solutions having concentrations lower than the cmc.

TABLE 1

| | | | | Example | | | | | | | | Comparative example | | | | | | | | |
|---|---|---|---|---|---|---|---|---|---|---|---|---|---|---|---|---|---|---|---|---|
| | | | | 1-1 | 1-2 | 1-3 | 1-4 | 1-5 | 1-6 | 1-7 | 1-8 | 1-1 | 1-2 | 1-3 | 1-4 | 1-5 | 1-6 | 1-7 | 1-8 | 1-9 |
| Treatment liquid | Composition (ppm) | (a) | a-1 | 100 | | | | 20 | | | | | | | | | | | | |
| | | | a-2 | | 100 | | | | 20 | | | | | | | | | | | |
| | | | a-3 | | | 100 | | | | 20 | | | | | | | | | | |
| | | | a-4 | | | | 100 | | | | 20 | | | | | | | | | |
| | | (a') | a'-1 | | | | | | | | | 100 | | | | 20 | | | | |
| | | | a'-2 | | | | | | | | | | 100 | | | | 20 | | | |
| | | | a'-3 | | | | | | | | | | | 100 | | | | 20 | | |
| | | | a'-4 | | | | | | | | | | | | 100 | | | | 20 | 20 |
| | Water | | | Balance | Balance | Balance | Balance | Balance | Balance | Balance | Balance | Balance | Balance | Balance | Balance | Balance | Balance | Balance | Balance | Balance |
| | pH (25° C.) | | | 6 | 6 | 6 | 6 | 6 | 6 | 6 | 6 | 6 | 6 | 6 | 6 | 6 | 6 | 6 | 6 | 6 |
| Evaluation | Adhesion amount of oil (mg/cm$^2$) | | | 1.4 | 0.0 | 0.1 | 0.4 | 2.0 | 0.2 | 0.4 | 0.9 | 4.5 | 4.3 | 4.1 | 3.7 | 9.1 | 9.0 | 3.4 | 3.5 | 5.2 |

TABLE 2

| | | | | Example | | | Comparative example | | | |
|---|---|---|---|---|---|---|---|---|---|---|
| | | | | 2-1 | 2-2 | 2-3 | 2-1 | 2-2 | 2-3 | 2-4 |
| Treatment liquid | Composition (ppm) | (a) | a-2 | 20 | 100 | | | | | |
| | | | a-3 | | | 100 | | | | |
| | | (a') | a'-2 | | | | 100 | | | |
| | | | a'-3 | | | | | 100 | | |
| | | | a'-5 | | | | | | 20 | |
| | | | a'-6 | | | | | | | 20 |
| | Water | | | Balance | Balance | Balance | Balance | Balance | Balance | Balance |
| | pH (25° C.) | | | 6 | 6 | 6 | 6 | 6 | 6 | 6 |
| Evaluation | Contact angle of oil droplet (°) | | | 80 | 82 | 80 | 1 | 1 | 12 | 15 |

(1) Anti-Staining Evaluation 1

A clean polypropylene plate (8 cm×3 cm, a surface energy of 26 mN/m) was placed in 300 mL of each of the treatment liquids of the compositions shown in Table 1, and while stirring the treatment liquid, 0.5 g of liquid paraffin was fed thereto. 60 seconds after feeding liquid paraffin, this plate was pulled up and dried, and the mass of the plate to which liquid paraffin adhered was measured. An increase in the mass of the plate before placing it in the treatment liquid and after adhering liquid paraffin to it was divided by the area of the front and back surfaces of the plate to determine a value used as the adhesion amount of oil (mg/cm$^2$). The results are shown in Table 1.

(2) Anti-Staining Evaluation 2

1 μL of triolein was adhered to a polypropylene plate, and the plate to which triolein was adhered was immersed in each of the treatment liquids of the compositions shown in Table 2. This treatment liquid was heated to a temperature of 50° C., and the contact angle of triolein was measured. The results are shown in Table 2. The results in Table 2 show that (3) Anti-Staining Evaluation 3

A clean polypropylene plate (8 cm×3 cm) was immersed in each of the treatment liquids of the compositions shown in Table 3 for 1 minute. After pulling up this plate from the treatment liquid, a portion 3 cm from the lower end of the plate was immersed in triolein and immediately pulled up, and the adhesion amount of oil (mg/cm$^2$) adhering to the portion immersed in triolein was determined. Specifically, the mass of oil adhering to the plate was determined from the difference in the mass of the plate before and after immersing it in triolein, and this mass of oil was divided by the area of both surfaces of the plate (3 cm×3 cm×front and back) to determine the adhesion amount of oil (mg/cm$^2$). The results are shown in Table 3. This result suggests that if hydrophobic surfaces are treated in advance with the anti-staining agent of the present invention, oil stains such as liquid oil or the like are thereafter less likely to adhere to the hydrophobic surfaces.

TABLE 3

| | | | | Example | | Comparative example | | | |
|---|---|---|---|---|---|---|---|---|---|
| | | | | 3-1 | 3-2 | 3-1 | 3-2 | 3-3 | 3-4 |
| Treatment liquid | Composition (ppm) | (a) | a-1 | 100 | | | | | |
| | | | a-2 | | 100 | | | | |
| | | (a') | a'-1 | | | 100 | | | |
| | | | a'-2 | | | | 100 | | |
| | | | a'-4 | | | | | 100 | |
| | | Water | | Balance | Balance | Balance | Balance | Balance | Balance |
| | pH (25° C.) | | | 6 | 6 | 6 | 6 | 6 | 6 |
| Evaluation | Adhesion amount of oil (mg/cm$^2$) | | | 9 | 6 | 12 | 13 | 13 | 15 |

The invention claimed is:

1. An anti-staining method, comprising:

reducing adsorption of a hydrophobic stain component to an object having a hydrophobic surface by contacting the object with a treatment liquid comprising a sulfosuccinic acid branched alkyl ester represented by formula (a1-1) as component (a) in an amount of 1 ppm or more and 500 ppm or less:

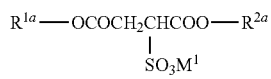
(a1-1)

where $R^{1a}$ and $R^{2a}$ are a 2-propylheptyl group and $M^1$ represents a hydrogen atom or a cation.

2. The anti-staining method according to claim 1, wherein the object is tableware.

3. The anti-staining method according to claim 1, wherein an automatic dishwashing machine is used to bring the treatment liquid into contact with the object.

4. The anti-staining method according to claim 1, wherein the treatment liquid has a pH of 2 or more and 10 or less.

5. The anti-staining method according to claim 1, wherein the treatment liquid has a temperature of 40° C. or more and 80° C. or less.

6. The anti-staining method according to claim 1, wherein the treatment liquid is brought into contact with the object by application, immersion, or spraying.

* * * * *